(12) United States Patent
Van Der Steen et al.

(10) Patent No.: US 8,454,520 B2
(45) Date of Patent: Jun. 4, 2013

(54) INTRAVASCULAR ULTRASOUND TECHNIQUES

(75) Inventors: Antonius Franciscus Van Der Steen, Rotterdam (NL); David Eric Goertz, Rotterdam (NL); Martijn Egbert Frijlink, Rotterdam (NL)

(73) Assignee: Stichting Voor De Technische Wetenschappen, Utrecht (NL)

( * ) Notice: Subject to any disclaimer, the term of this patent is extended or adjusted under 35 U.S.C. 154(b) by 692 days.

(21) Appl. No.: 11/660,301

(22) PCT Filed: Aug. 11, 2005

(86) PCT No.: PCT/EP2005/008797
§ 371 (c)(1),
(2), (4) Date: Jan. 9, 2008

(87) PCT Pub. No.: WO2006/015877
PCT Pub. Date: Feb. 16, 2006

(65) Prior Publication Data
US 2008/0200815 A1  Aug. 21, 2008

(30) Foreign Application Priority Data

Aug. 13, 2004 (GB) .................................. 0418118.6

(51) Int. Cl.
*A61B 8/14* (2006.01)
(52) U.S. Cl.
USPC ........... 600/467; 600/466; 600/462; 600/437; 600/407
(58) Field of Classification Search
USPC .................. 600/437, 407, 466, 467, 462, 459
See application file for complete search history.

(56) References Cited

U.S. PATENT DOCUMENTS

| 5,115,814 | A | * | 5/1992 | Griffith et al. | ................ 600/463 |
| 5,203,337 | A | * | 4/1993 | Feldman | ....................... 600/463 |
| 5,203,338 | A | | 4/1993 | Jang | |
| 5,203,992 | A | | 4/1993 | Drouen | |

(Continued)

FOREIGN PATENT DOCUMENTS

| JP | H11253449 A | 9/1999 |
| JP | 2002102229 A | 4/2002 |
| JP | 2002522133 A | 7/2002 |

OTHER PUBLICATIONS

International Search Report, Nov. 14, 2005, PCT/EP2005/008797.

(Continued)

*Primary Examiner* — Tse Chen
*Assistant Examiner* — Joel F Brutus
(74) *Attorney, Agent, or Firm* — Stout, Uxa, Buyan & Mullins, LLP

(57) ABSTRACT

Intravascular ultrasound techniques provide for intravascular imaging using contrast agents and nonlinear techniques. An ultrasound imaging device for detecting internal properties of a target body comprises an ultrasound transducer positioned at a distal end portion of a catheter, for transmitting excitation pulses and for receiving echo signals. A signal processor analyses echo signals at harmonics and/or subharmonics of the transmit frequency. The catheter may include a contrast agent delivery conduit extending along the catheter, the delivery conduit having an exit orifice proximal to the ultrasound transducer. The device may discriminate between echo signals respectively arising from interaction with tissue and from the interaction with contrast agent. The device may generate an image of the site of interest using non-linear components of the received ultrasound echo signals.

25 Claims, 5 Drawing Sheets

U.S. PATENT DOCUMENTS

| | | | |
|---|---|---|---|
| 5,476,100 A * | 12/1995 | Galel | 600/466 |
| 5,531,679 A | 7/1996 | Schulman et al. | |
| 5,549,111 A * | 8/1996 | Wright et al. | 600/443 |
| 5,749,364 A * | 5/1998 | Sliwa et al. | 600/438 |
| 5,797,858 A | 8/1998 | Rourke | |
| 5,833,615 A * | 11/1998 | Wu et al. | 600/458 |
| 5,840,031 A * | 11/1998 | Crowley | 600/440 |
| 5,848,969 A | 12/1998 | Panescu et al. | |
| 5,947,904 A * | 9/1999 | Hossack et al. | 600/458 |
| 6,066,096 A * | 5/2000 | Smith et al. | 600/439 |
| 6,287,271 B1 * | 9/2001 | Dubrul et al. | 604/22 |
| 6,321,109 B2 * | 11/2001 | Ben-Haim et al. | 600/424 |
| 6,423,002 B1 | 7/2002 | Hossack | |
| 6,443,894 B1 * | 9/2002 | Sumanaweera et al. | 600/443 |
| 6,612,992 B1 | 9/2003 | Hossack et al. | |
| 6,645,147 B1 | 11/2003 | Jackson et al. | |
| 7,025,726 B2 * | 4/2006 | Porter et al. | 600/458 |
| 2003/0208123 A1 | 11/2003 | Panescu | |
| 2004/0030250 A1 | 2/2004 | Stewart | |
| 2004/0049148 A1 * | 3/2004 | Rodriguez et al. | 604/22 |
| 2004/0181206 A1 * | 9/2004 | Chiu et al. | 604/509 |
| 2005/0124895 A1 * | 6/2005 | Jensen et al. | 600/453 |
| 2005/0125002 A1 * | 6/2005 | Baran et al. | 606/108 |

OTHER PUBLICATIONS

Van Der Steen A F W et al: "IVUS harmonic imaging", Ultrasound Med BIOL; Ultrasound in Medicine and Biology 2000 Elsevier Science Ltd, Exter, Engl, vol. 26, No. suppl. 2, 2000. p. A90, XP002351397 the whole document.

Foster F S: "Transducer Materials and Probe Construction", Ultrasound in Medicine and Biology, New Yourk, NY, US, vol. 26, May 2000. pp. S2-S5, XP004295543; ISSN: 0301-5629: p. S2, first column, line 21-24; p. S5, section 'Conclusions'.

Frijlink M E et al: "High frequency harmonic imaging in presence of intravascular stents" IEEE Ultrasonics Symposium (IEEE CAT. No. 03CH37476) Piscataway, NJ, USA, vol. 1, 2003, pp. 208-211, XP002351398, ISBN: 0-7803-7922-5 cited in the application p. 209, section III. 'Results', first paragraph.

Hirooka et al. "Contrast-Enhanced Endosonography: Fundamental Principles and Clinical Significance" Endoscopica Digestiva, Tokyo Igakusya Ltd., Japan vol. 15, No. 8, Aug. 25, 2003, pp. 1055-1062.

* cited by examiner

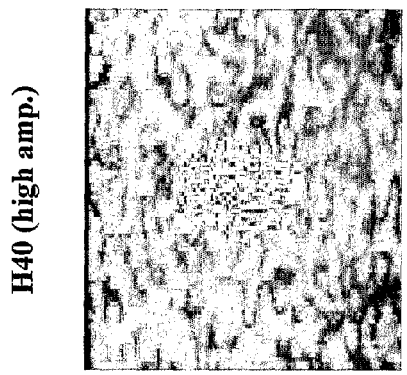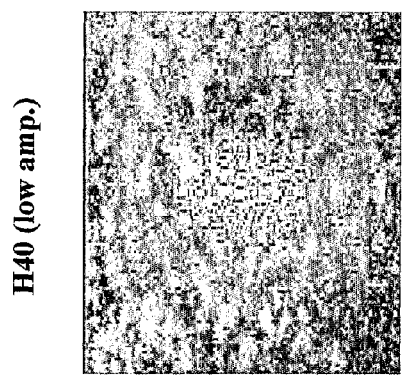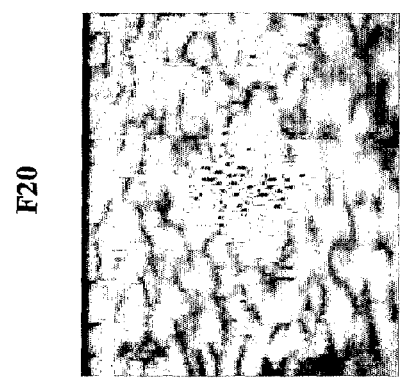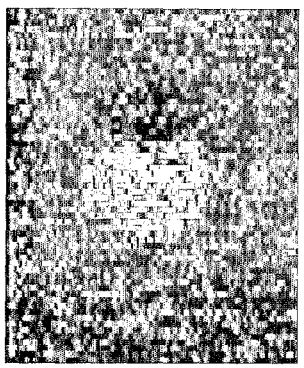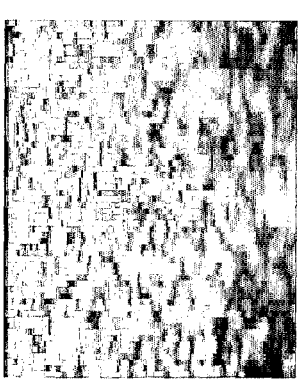
Fig. 3
Fig. 4

INTRAVASCULAR ULTRASOUND TECHNIQUES

The present invention relates to methods and apparatus for ultrasound detection and imaging in intravascular applications.

Currently, the decision to revascularize a symptomatic cardiac patient is based on the severity of a coronary luminal obstruction caused by atherosclerotic plaque formation. However, the arterial wall may also contain atherosclerotic lesions, which have not resulted in arterial lumen narrowing. Around 40% of acute cardiovascular events, including fatal or non-fatal myocardial infarction or stroke, are thought to be caused by sudden rupture events that occur in these plaques. Plaque vulnerability is known to be related to its composition, stress distribution, and inflammation. Increasingly, it is becoming recognized that two other factors are linked to plaque progression: a) the microvascular status of the plaques (vasa vasorum); and b) the expression of specific molecules within the plaques.

Vasa vasorum are the microvessels that supply blood to cells within the walls of larger blood vessels that lie beyond the diffusion limit for nutrient and waste exchange with the vessel lumen. While their precise role is not entirely understood, evidence is mounting that the growth of neovascular vasa vasorum through the process of angiogenesis is a crucial step in the development of atherosclerotic plaques. This realization has led to an emerging interest in the vasa vasorum as a therapeutic target. Further, these new plaque-associated microvessels appear to have a different density and spatial distribution than in normal coronary arteries, which suggests the possibility that they may be an independent marker for plaque staging. Due to the small vessel sizes, slow blood flow, and large tissue motion, this presents a very challenging problem for imaging. Currently there is no clinically available technique capable of imaging vasa vasorum in the coronary arteries.

Molecular imaging is a rapidly evolving area of medical imaging that is anticipated to have a substantial impact on the diagnosis and treatment of a range of disease processes. The general imaging approach is to introduce particles (e.g. bubbles or droplets) into the body, which can be detected with a medical imaging modality (e.g. magnetic resonance imaging, positron emission tomography or ultrasound), and which have been treated in such a way as to adhere to specific molecules that are only present in regions of diseased tissue or cells. It is of primary importance to the success of molecular imaging with a given modality that the targeted agent be detected with sufficient sensitivity and specificity.

The majority of ultrasound systems operate at frequencies in the 1 to 10 MHz range and form images using a hand-held transducer that is external to the body. Such systems are capable of providing real-time information about tissue structure, and blood flow in the heart and larger vessels. Unfortunately, microvessel detection and mapping is not possible at these frequencies due to low signal strengths from blood, tissue motion effects, and limited spatial resolution.

Microvessel detection with ultrasound can be improved by increasing the operating frequency, due in large part to increases in ultrasound scattering from blood at higher frequencies. However, increased signal attenuation at higher frequencies requires that the transducer is located close to the region of interest, i.e. closer than approximately 5 or 10 mm at 50 MHz. Experimental microvessel flow imaging systems operating in the 20 to 50 MHz range have hitherto therefore only examined superficial tissues such as the eye, skin and superficial tumors. Regardless of frequency, tissue motion effects inhibit the detection of microvessels.

Intravascular ultrasound (IVUS) is an established tool for gaining insight into the size, structure, and composition of atherosclerotic plaques. Intravascular ultrasound (IVUS) is a method by which a catheter-based high frequency (20 to 50 MHz) transducer is used to create high-resolution images of the lumen and vascular wall of larger vessels. It is an established interventional cardiology tool for gaining insight into the size, structure, and composition of atherosclerotic plaques. Techniques have also been developed to assess flow within the lumen of larger vessels (>2 mm diameter) using IVUS. However, no existing IVUS system or technique has been capable of imaging blood flow in the vasa vasorum.

Within the last two decades, gas bubbles of micrometer size have been employed in 1 to 10 MHz ultrasound systems to improve the quality of cardiovascular images and thereby improve the quality of medical diagnosis. Gas bubbles are typically stabilized using emulsifiers, oils, thickeners or sugars, or by entraining or encapsulating the gas or a precursor thereof into a variety of systems. Stabilized gas bubbles are generally referred to as "gas-filled microvesicles" or microbubbles. Examples of microbubbles include gas bubbles dispersed in an aqueous medium and stabilized at the gas/liquid interface by a very thin envelope involving a surfactant (i.e., an amphiphilic material). These microvesicles are prepared by contacting powdered amphiphilic materials, e.g. freeze-dried preformed liposomes or freeze-dried or spray-dried phospholipid solutions, with air or other gas and then with an aqueous carrier, and agitating to generate a microbubble suspension which is then administered shortly after its preparation.

Other examples of gas-filled microvesicles are suspensions in which the gas bubbles are surrounded by a solid material envelope of natural or synthetic polymers, lipids, proteins or mixtures thereof. These microvesicles are in general referred to in the art as "microcapsules" or "microballoons", while the term "microbubbles" refers more commonly to surfactant-stabilized microvesicles. For the sake of clarity, in the present description and claims, the terms "bubble", "microbubble", and gas-filled microvesicle, where not expressly mentioned, are used interchangeably.

Examples of suitable aqueous suspensions of gas-filled microvesicles and of the preparation thereof are disclosed, for instance, in U.S. Pat. No. 5,271,928, U.S. Pat. No. 5,445,813, U.S. Pat. No. 5,413,774, U.S. Pat. Nos. 5,556,610, 5,597,549, U.S. Pat. No. 5,827,504, U.S. Pat. No. 5,711,933, U.S. Pat. No. 6,333,021, WO 97/29783 and WO 2004/069284, all incorporated herein by reference.

These bubbles, referred to as contrast agents, are small enough to pass safely through the capillaries, and are introduced into the body through injection. During the formation of an ultrasound image, the bubbles are stimulated to produce acoustic emissions that are distinct from those of tissue, which are then exploited with specific imaging strategies to form images of the vasculature. Most current imaging strategies rely upon nonlinear bubble behaviour, which occurs when bubbles are stimulated with sufficient amplitude with ultrasound frequencies related to the bubble resonant frequency. The resonant frequency is related to bubble size, and most contrast agents are comprised primarily of bubbles in the 1 to 10 micron range in order to exhibit resonant behaviour in the conventional ultrasound frequency range.

Most implementations of nonlinear bubble imaging exploit second harmonic emissions (centred at or near twice the transmit frequency) emissions, though the efficacy of this approach for separating blood and tissue signals can be confounded by the presence of tissue propagation harmonics. A variety of other approaches have also been examined, including subharmonic imaging, which in the case of contrast agents has been centred about half the transmit frequency (the order half subharmonic) [1]. Nonlinear energy may also be distributed in other frequency regions, through a variety of mechanisms such as, for example, spectral broadening, transient responses and bubble disruption. Initial implementations of nonlinear bubble imaging relied upon separation of linear and nonlinear signals largely through frequency domain filtering. Subsequently multipulse techniques were developed, such as phase and amplitude modulation schemes. Bubbles may also be destroyed, which has enabled the implementation of ultrasound destruction-reperfusion techniques for assessing tissue perfusion. Detection of bubbles during destruction also can be used. The application of microbubble contrast agents in combination with specific detection techniques has enabled the detection of blood located in microvessels in many clinically relevant situations.

There is a growing interest in developing molecular imaging techniques in medical ultrasound through the use of targeted microbubbles [2].

Little work has been done with microbubble contrast agents at transmit frequencies above 15 MHz. Demos et al [3] showed the detection of targeted gaseous liposomes with RVUS in animal models of thrombus. Cachard et al [4] visualized microbubbles with IVUS in an in vitro detection for the purposes of enhancing visualisation of lumen boundaries. Moran et al [5] conducted a study of the linear scattering properties of four agents in the 30 MHz frequency range with IVUS. Deng et al [6] performed imaging of microbubbles within microvessels situated in the anterior segment of a rabbit eye. Preliminary studies have illustrated the ability of microbubbles to enhance the signal strength from blood in high frequency colour flow imaging [7], [8] experiments. All of this work has examined or assumed linear scattering from microbubbles at high frequencies.

Commercially available contrast agents are not designed for use at high frequencies. As bubbles are reduced in size, oscillation damping increases and it is generally accepted that nonlinear oscillations associated with resonant bubble behaviour are more difficult to initiate. It is theoretically predicted that there will be an upper limit to resonant frequency as bubbles are decreased in size [9]. However, it has recently been shown that it is possible to initiate nonlinear scattering (subharmonics, ultraharmonics and second harmonics) from a commercially available agent (Definity™) at transmit frequencies in the 14 to 32 MHz range [10], [11]. In vivo microvessel detection in animals has also been demonstrated using the subharmonic of a 20 MHz transmit frequency using Definity™ [12]. Second harmonic imaging mode did not show improvements in contrast agent detection due to the presence of high levels of tissue second harmonic signals. These results for nonlinear imaging at high frequencies were achieved with a type of transducer (spherically focused polymer film transducer) that can only be used external to the body due to its size (typically 6 to 12 mm in diameter). Such transducers are well suited to nonlinear imaging since they are broad bandwidth (>100%) and can achieve high pressures through focusing. This technology is appropriate for use with small animal imaging, dermatology and ophthalmology.

Nonlinear tissue imaging techniques have also been developed. In this case nonlinear propagation of ultrasound, (increasing with transmit pressure) gives rise to harmonics (centred at positive integer multiples of the transmit frequency). IVUS transducer elements (not catheter based) have been shown to be capable of producing second harmonic images, with nonlinear signals isolated with analog filtering and signals being averaged at a series of discrete transducer beam locations [13], [14].

It is an object of the present invention to facilitate detection of vasa vasorum and plaque-associated molecules using ultrasound techniques. It is a further object of the present invention to facilitate the use of nonlinear contrast microbubble imaging with IVUS. It is a further object of the present invention to facilitate the use of nonlinear tissue harmonic imaging with IVUS. It is a further object of the invention to improve the image quality of IVUS using tissue harmonic imaging by using multiple pulse sequences.

According to one aspect, the present invention provides an ultrasound imaging device for detecting internal properties of a target body, comprising: an ultrasound transducer positioned at a distal end portion of a catheter for intravascular introduction into the target body, the ultrasound transducer having a transmit frequency; a waveform generator, coupled to the transducer, for producing excitation pulses at said transmit frequency; a receiver for receiving echo signals from the transducer; and a signal processor for analysing echo signals at harmonics and/or subharmonics of the transmit frequency.

According to another aspect, the present invention provides an ultrasound imaging device for intravascular ultrasound imaging of a patient's body comprising: a catheter-based ultrasound transducer for insertion into the body at a site of interest; means for transmitting a series of ultrasound excitation signals from the transducer sufficient to induce a non-linear response in tissue at the site of interest; means for receiving ultrasound echo signals in response to the excitation signals; and means for generating an image of the site of interest using non-linear components of the received ultrasound echo signals.

According to another aspect, the present invention provides an ultrasound transducer head for use with an intravascular ultrasound imaging system for imaging internal parts of a target body, comprising: an ultrasound transducer positioned at a distal end portion of a catheter for intravascular introduction into the target body; and a contrast agent delivery conduit extending along the catheter, the delivery conduit having an exit orifice proximal to the ultrasound transducer.

Embodiments of the present invention will now be described by way of example and with reference to the accompanying drawings in which:

FIG. 3 shows exemplary images of selectively located contrast agent bubbles produced using: (a) 20 MHz fundamental frequency imaging; (b) 40 MHz harmonic imaging from low amplitude excitation; and (c) 40 MHz harmonic imaging from high amplitude excitation;

FIG. 4 shows exemplary images of selectively located contrast agent bubbles produced using: (a) 40 MHz fundamental frequency imaging; and (b) 20 MHz subharmonic imaging;

Figure 7:
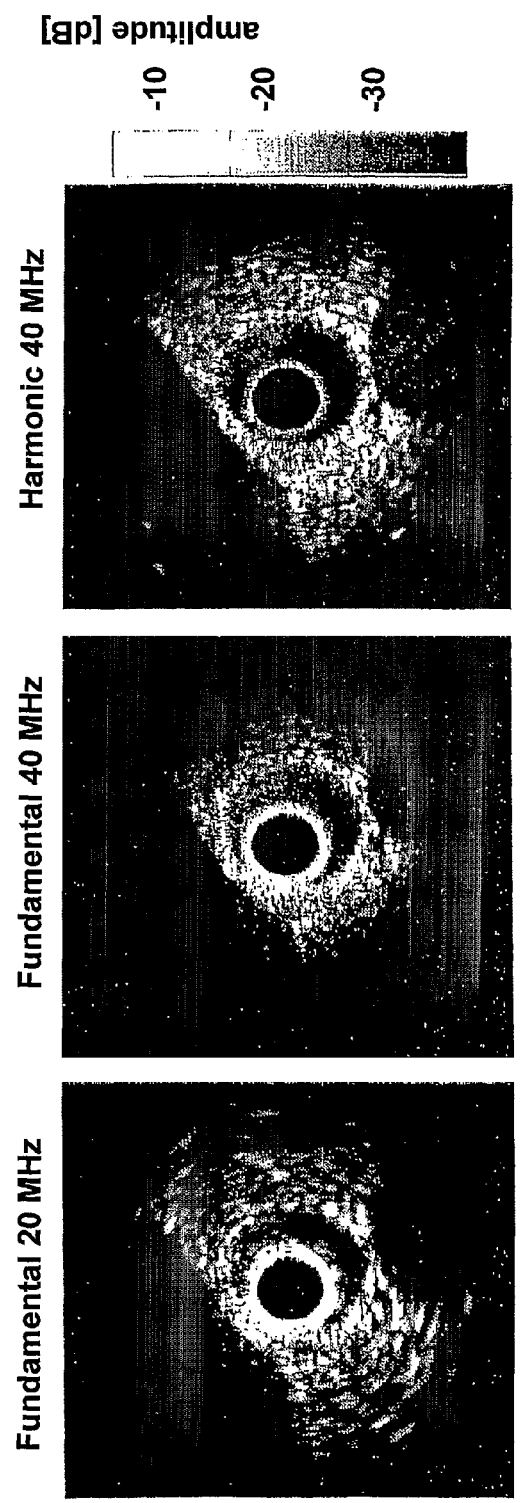

MHz mode, the fundamental 40 MHz mode and the 40 MHz harmonic mode from a catheter-based rotating single element transducer; and FIG. 7 shows exemplary images of cross-sections of an atherosclerotic rabbit aorta acquired with the fundamental 20 MHz mode, the fundamental 40 MHz mode and the 40 MHz harmonic mode from a catheter-based single element transducer.

Conventional IVUS operates with ultrasound in the 20 to 50 MHz range, which extends beyond the range of reported nonlinear oscillations for contrast agents. According to currently published data, there is no indication that nonlinear scattering is possible at transmit frequencies above 32 MHz. The isolation of bubbles below 1 micron in diameter produces improved second harmonic and subharmonic generation for a transmit or excitation frequency of 30 MHz [15]. The peak transmit pressure used to initiate subharmonics in [15] was 3.2 MPa. While subharmonic generation is not well understood at these frequencies, it is reasonable to expect that pressures required to initiate subharmonics will increase with transmit frequency.

Existing IVUS technology has significant constraints. Intravascular ultrasound is necessarily a catheter-based technique and as such very small aperture transducers are used. Current IVUS systems employ either a mechanically rotated single element transducer, or an electronically steered array transducer. Mechanical rotation systems employ unfocussed transducers of <1 mm radiating surface, and images are formed from single pulses along a series of beam directions. These transducers have limited bandwidths. Due to the transducer location at the tip of a catheter approximately 1.5 m long, there can be electrical tuning effects which narrow the effective bandwidth on transmit and reception still further. IVUS array transducers are even more narrowband than single element transducers, and obtain lower pressures. These constraints limit the ability of IVUS to initiate and detect nonlinear signals. The transmit pulse and receive pulse must both be within the pass band of the transducer, which limits the pressure that can be achieved on transmit, limits the signal bandwidth, and results in loss of received acoustic energy.

To date, no targeted or untargeted nonlinear (or bubble specific) microbubble imaging has been reported with IVUS systems. No reports have been made for tissue harmonic imaging with a mechanically rotating IVUS catheter or an array catheter. Implementing second harmonic microbubble imaging in IUS requires operation at a frequency range where second harmonic contrast images have not been successfully demonstrated as a means to improve contrast agent to tissue signals. The application of multipulse techniques such as pulse-inversion to isolate nonlinear signals in the context of a rapidly rotating transducer has not been demonstrated and can be expected to suffer from signals decorrelation effects between pulses. For subharmonic imaging, achieving transmit pressures indicated in the above literature (e.g. [15]) at the upper range of the transducer bandwidth may not be feasible.

The inventors have established that a contrast agent comprising bubbles below 1 micron in diameter can be used to effectively produce detectible nonlinear emissions at least up to 40 MHz, and under conditions (e.g. sufficiently low pressures) that are feasible to achieve with IVUS techniques.

The inventors have also determined that nonlinear detection, at high frequencies, of microbubble contrast agents bound to a surface is also possible, despite the different physical conditions experienced by bound and free bubbles.

The inventors have also determined that nonlinear detection of tissue harmonic signals can be isolated, and second harmonic images thereby formed, by means of multiple pulse methods, like pulse-inversion methods during the rotation of a mechanically steered IVUS catheter.

Figure 1:
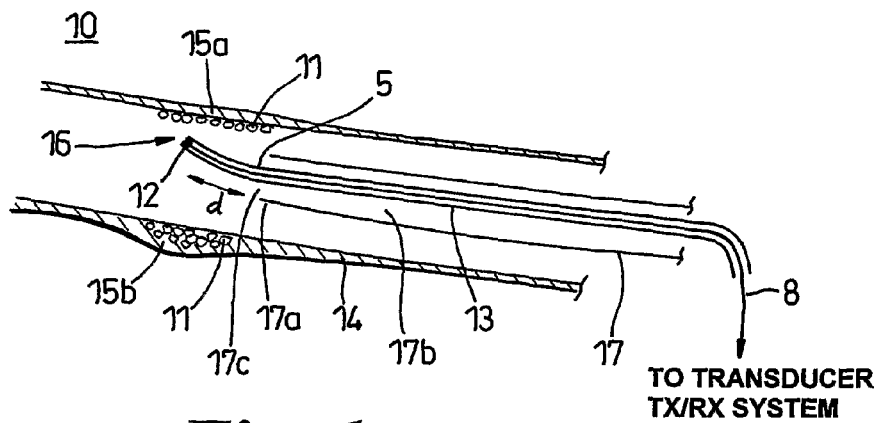
FIG. 1 is a schematic diagram of a catheter-based intravascular ultrasound system in situ in the body at a region of interest.

With reference to FIG. 1, in a preferred arrangement, intravascular ultrasound imaging in a patient's body 10 provides for detection of encapsulated gaseous acoustic contrast agent 11 with intravascular ultrasound. It will be understood that other types of contrast agent particle may be used as the contrast agent 11. Specific acoustic signals are induced and detected from the encapsulated gas bubbles 11 using an intravascular ultrasound transducer 12. The induction and detection of nonlinear bubble oscillations is used to distinguish ultrasound echo signals arising from tissue (including blood) from echo signals arising from contrast agent particles.

The ultrasound excitation signal transmitter and echo signal receiver comprises a transducer 12 mounted on a catheter 13 or guidewire introduced through a vessel 14 such as the coronary artery. In preferred arrangements, the length of the catheter is in the range 60 to 200 cm (only partial length is shown in the figure) and the outer diameter is in the range 0.7 to 3 mm.

In one arrangement, a bend 5 may be formed in the distal end region of the catheter, approximately 15 to 30 mm from its tip, to provide lateral displacement of the transducer 12 to a position off the main axis of the catheter 13 and thereby closer to the walls of the vessel 14. The transducer 12 communicates with transmit and receive electronics via wiring 8 passing through the catheter 13.

The transducer 12 may be used to excite and detect free contrast agent that is located in the main vessel lumen (in which the IVUS is situated), in side-branches of the main lumen, in vasa vasorum, and in other vessels or microvessels within the surrounding tissue.

The transducer 12 may be used to excite and detect free contrast agent 11 that has selectively located to a region 15a of specific character, e.g. the vasa vasorum. The transducer 12 may be used to excite and detect targeted contrast agent 11 that has selectively located to target plaque-associated molecules 15b (including molecules expressed by vasa vasorum) or to markers related to neovascularisation. The transducer 12 may be used to excite and detect targeted contrast agent 11 that has selectively located to target molecules 15b associated with other vascular diseases.

The contrast agent 11 (which expression includes free bubbles) preferably comprises encapsulated bubbles that are of a composition and a size distribution capable of oscillating in a nonlinear manner at intravascular ultrasound transmit centre frequencies of at least 10 MHz, preferably in the range 10 to 80 MHz, and more preferably in the range 15 to 60 MHz, and more preferably with centre frequency above 15 MHz or above 30 MHz.

Preferably, the contrast agent bubbles 11 have compliant shells encapsulating a gaseous medium. Preferably, the contrast agent bubbles 11 are gas-filled microvesicles stabilised by a surfactant, and in particular a phospholipid. Preferably, the contrast agent includes a substantial proportion of bubbles having diameters less than 1.5 microns, more preferably less than 1.0 microns, and still more preferably of diameters in the range of 0.2 to 1.5 microns. Preferably bubbles with diameters in the specified ranges (e.g. 0.2 to 1.5 microns) form greater than 1% of the volume fraction, more preferably greater than 2% of the volume fraction, even more preferably greater than 5% of the volume fraction, and still more preferably greater than 10% of the volume fraction. According to further preferred embodiments, the bubbles form greater than 50% of the volume fraction, and more preferably greater than 70% of the volume fraction.

These contrast agent bubbles 11 can be specifically manufactured to achieve such a size distribution. A suitable method for preparing bubbles with the desired high volume fractions in the specified ranges is disclosed in WO 2004/069284. Alternatively, existing commercially available contrast agent designed for use at lower frequencies but having a significant number of smaller bubbles can have its population distribution modified to some extent by decantation or mechanical filtration [13].

The contrast agent bubbles 11 are preferably introduced into the blood stream either through a systemic steady infusion or in the form of a bolus. The steady state infusion may be administered through a systemic intravenous drip, as can be done for conventional frequency contrast agent use. The contrast agent may be introduced in combination with localised drug delivery. For the avoidance of doubt, the expression "introducing contrast agent into the vicinity of the transducer" is intended to encompass both (i) 'local' introduction of the contrast agent at or very close to the transducer location, and (ii) 'remote' introduction of the contrast agent elsewhere in the body, relying on transport of the agent to the vicinity of the transducer using inherent action of the body, such as blood flow.

More particularly, as shown in FIG. 1, the IVUS catheter 13 carrying the transducer 12 at an imaging tip 16 may be introduced into the vessel of interest 14 within a sheath or delivery catheter 17. When located at the region or site of interest, the imaging tip 16 extends past the end 17a of the sheath 17 by a distance d which is preferably variable or pre-selectable. In preferred arrangements, the distance d is in the range 10 to 300 mm. Contrast agent 11 may be injected locally though the sheath 17, which defines a delivery conduit 17b, to an exit orifice 17c at or proximal to the end 17a. This facilitates the delivery of a high local concentration of contrast agent 11 at the site of interest.

Near the imaging tip 16 there may be an outward taper (not shown) of the entire catheter 13 or of its inner diameter to reduce the space between the outer diameter of the catheter 13 and the inner diameter of the delivery catheter or sheath 17 to avoid pre-injection leakage. Preferably, the exit orifice 17c will be formed as openings in the periphery of the delivery catheter 17 so as to permit the exit of contrast agent in a manner that encourages an even agent distribution towards the vessel wall 14. The exit orifice 17c openings may preferably be provided within about 10 cm of the end of the sheath 17.

A suitable remotely controllable closure mechanism (not shown) may be provided to open and close the exit orifice 17c, e.g. using a control wire so that the timing of contrast agent delivery can be carefully controlled.

Although in the illustrated embodiment, the IVUS catheter 13 and its transducer 12 is integrated with the delivery conduit 17b by incorporation within the delivery sheath, it will be understood that the roles may be reversed with the delivery conduit 17b being formed within the IVUS catheter. In a further arrangement, the IVUS catheter 13 and delivery sheath 17 may be integrated by coupling them together side-by-side.

The catheter-based transducer 12 may of any suitable type, e.g. comprising one or more layers of active or passive components and acoustic matching and backing layers. The frequency response of the transducer may have a single frequency region of efficiency or a combination or multiple peaks of efficiency. In one configuration, the transducer may have elevated efficiency around the transmitted frequency and at an integer number times this transmitted frequency and in another configuration at the transmitted frequency and at half of this frequency. In one configuration, the transducer 12 may comprise an array of transducer elements which are capable of producing an electronically steerable ultrasound excitation beam. In another configurations, the transducer 12 may comprise a mechanically manipulable single or multiple element transducer so that the direction of excitation beam can be steered or scanned during a sequence of excitation pulses.

The transducer 12 is adapted to be capable of generating acoustic excitation pulses of sufficient pressure and other characteristics (e.g. length, frequency content) to initiate non-linear scattering or response from the contrast agent.

Figure 2:
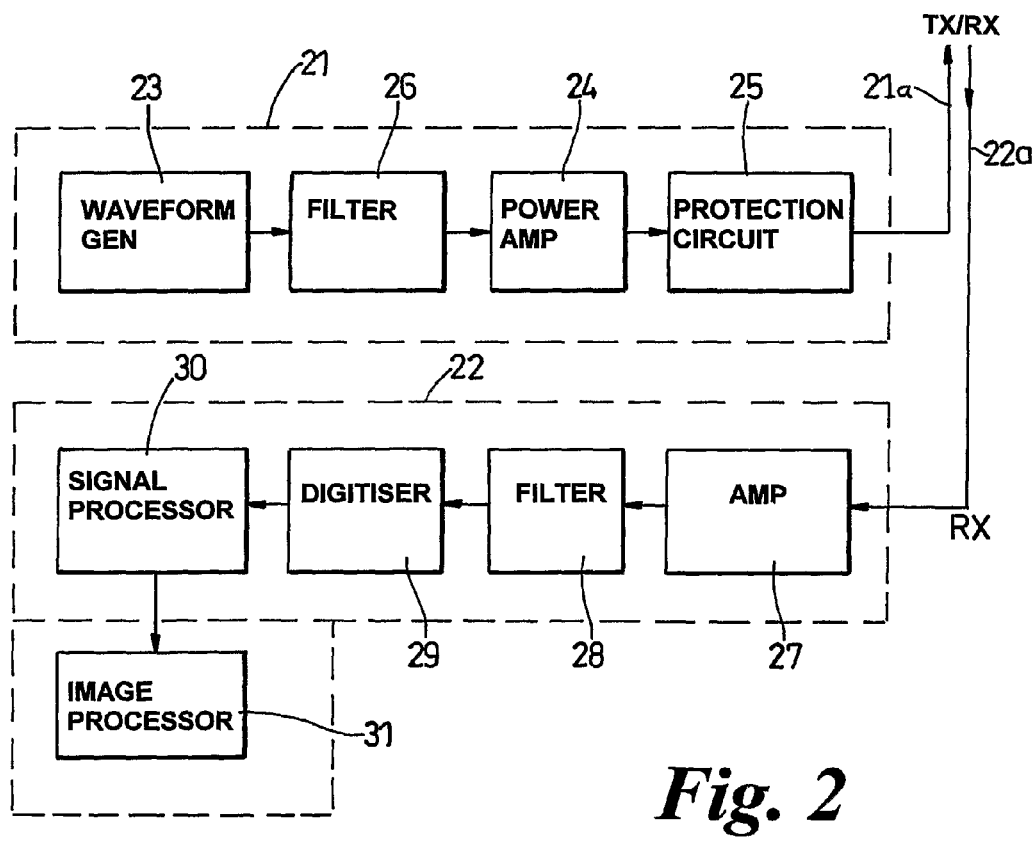
FIG. 2 is a schematic diagram of transmit and receive subsystems for use with the catheter-based intravascular ultrasound transducer of FIG. 1.

With reference to FIG. 2, a transmit subsystem 21 is provided to generate sequences of excitation pulses 21a of sufficient amplitude characteristics (e.g. length, frequency content) to the transducer 12 in order to initiate the nonlinear scattering in the contrast agent. Part of the transmit subsystem may reside within the catheter 13.

Preferably, the excitation pulses are generated at frequencies greater than 10 MHz, more preferably at frequencies greater than 15 MHz. Preferably, the excitation pulses have centre frequencies in the range 10 to 80 MHz and more preferably in the range 15 to 60 MHz. In other embodiments, the excitation pulse centre frequency is in the range 15 to 50 MHz, and more preferably 15 MHz or higher, or above 30 MHz.

Pulse sequences may be phase- and/or amplitude-modulated or frequency-band limited in order to sufficiently permit the isolation of bubble-specific scattering after reception of echo signals arising from interaction of the excitation signals with the tissue and with the contrast agent. In general, any excitation pulse characteristic may be used to enable or enhance the ability to discriminate between echo signals respectively arising from interaction of ultrasound excitation signals with tissue and interaction with contrast agent.

The sequence of excitation pulses may comprise pulses that are identical, that vary in amplitude, that vary in phase or that vary in length. Pulses may be derived from combinations of previously transmitted pulses, e.g. inverted copies and the like.

Excitation pulses may be adapted to be used to destroy contrast agent, and to detect agent during the destruction thereof, or to use imaging pulses which follow destruction pulses. Part of the transmit subsystem 21 may reside within the catheter 13.

Detection of nonlinear bubble behaviour may be achieved by way of detection of echo pulses of sufficient bandwidth, in the form of single or multiple frequency peaks, or through energy loss in the receive bandwidth or through the detection of transient bubble responses.

With further reference to FIG. 2, a receive subsystem 22 conditions received echo signals 22a from the transducer (e.g. by amplification and filtering), digitizes the conditioned signal in a manner compatible with separating the tissue and blood signals (e.g. with sufficient phase coherence). Part of the receive subsystem 22 may reside within the catheter 13 which may have benefit with respect to overcoming electrical tuning effects and improving signal to noise ratio. Part of the system may be provided by a personal computer. Preferably, the receive subsystem is adapted to receive echo signals in at least a part of the range 8 to 80 MHz.

A signal processor 30 and an image processing subsystem 31 may be used to apply appropriate algorithms to extract bubble specific signals and thereby form images that have improved sensitivity and specificity to the contrast agent. It is to be understood that free bubbles located in vasa vasorum or targeted bubbles located anywhere may have specific acoustic signatures that may be exploited in transmission of excitation signals, in reception of echo signals and in signal processing.

In one preferred embodiment, the echo signal analysis and imaging is performed on echo signals in a frequency band that is different to but potentially overlapping or non-overlapping with that of the transmit frequency band. In one arrangement, the echo signal analysis and imaging is performed on echo signals in a frequency band comprising the second harmonic of a transmit frequency. In another arrangement, the echo signal analysis and imaging is performed in a frequency band comprising a subharmonic of a transmit frequency. In another arrangement, both harmonics and subharmonics are used in the echo signal analysis and imaging.

In preferred embodiments, subharmonic imaging from excitation signals having centre frequencies in the range 20 to 60 MHz is preferred, requiring for example acoustic pressures of at least 50 kPa.

In order to initiate and detect nonlinear ultrasound signals using an intravascular transducer system as shown in FIG. 1, it is necessary to achieve sufficient acoustic pressure in the excitation signals and provide sufficient bandwidth and/or sensitivity when receiving the echo signals.

Preferably, very thin transducer layers are deployed to resonate at high frequencies, and small aperture dimensions of less than 1 mm to fit in suitable catheters 13.

Nonlinear oscillations in contrast agent may be detected by signal changes primarily within the transmit frequency bandwidth. One approach for doing this is to employ power modulation approaches. In power modulation, the transmit amplitude of successive excitation pulses is varied, to result in differences in nonlinear signal generation (and thereby a corresponding reduction in the echo signals present in the transmit bandwidth). On receiving echo signals, pulse groups are combined in such a way as to extract the nonlinear signal strength by analyzing differences in the transmit bandwidth. Other approaches are also possible, for example exploiting the transient response of contrast agent.

Differentiation between contrast agent bubbles within the main vessel lumen 14 (e.g. the coronary vessel) and bubbles within vasa vasorum 15a situated in tissue immediately adjacent to the lumen 14 may be effected by using correlation-based techniques to differentiate between slowly moving bubbles 11 in the vasa vasorum 15a and more rapidly moving bubbles in the lumen 14. This may be done within a given image frame and/or between two or more consecutive image frames (frame rate is typically 20 to 30 frames per second).

If a local upstream bolus injection is used to introduce the contrast agent, this will result in a rapid passage of agent within the main lumen 14, followed by a time-delayed arrival of agent to the vasa vasorum. Analyzing the evolution of the signals in a region of interest (ROI) as a function of time after a bolus may therefore assist in discriminating between contrast agent in the main lumen and agent in the vasa vasorum. Such approaches may use frame-to-frame image tracking due to tissue motion.

Destruction-reperfusion techniques may also be used. In such techniques, a series of narrow bandwidth pulses (preferably at as low a frequency as achievable) is more appropriate to achieve destruction of the contrast agent bubbles. Imaging pulses may then follow. Two different transducers may be used within the catheter located at or near the imaging tip 16: a first transducer for destructive excitation pulses (e.g. with a frequency in the range 1 to 15 MHz, and preferably in the region of 5 MHz) and a second transducer for imaging, of the type described above. Imaging may be performed during destruction, or during reperfusion.

Either transducer may be used to facilitate the targeting of contrast agent by means of radiation pressure. In a preferred embodiment acoustic pulses will be sent out in such a way as to enhancement binding following the injection of agent. This will then be followed by pulse sequences that are appropriate for imaging the bound agent.

Targeted and untargeted contrast agent bubbles may be differentiated using a number of techniques. Correlation-based techniques may be used to differentiate between bound and free bubbles. These techniques may be performed within a given frame and/or between two or more consecutive frames (frame rate is typically 20 to 30 frames per second). Such approaches may use frame-to-frame image tracking. Destruction techniques may be used, as previously described above. Imaging may be performed during destruction, or during re-accumulation at target sites. Differences between the acoustic response of bound and free bubbles located within the lumen may also be used.

With further reference to FIG. 2, an exemplary demonstration of the ultrasound imaging is now described. In the transmit subsystem 21, a waveform generator 23 provides a suitable pulse waveform to a power amplifier 24, to generate excitation signals from the transducer 16. Protection circuitry 25 in the form of an expander/limiter may be provided at the output of the power amplifier 24. A transmit-side filter 26 may be provided to pre-condition waveforms generated by the waveform generator 23. It will be understood that any or all of the elements 23-26 of the transmit subsystem 21 could be combined and/or incorporated into a single electronic circuit.

In the receive subsystem 22, an amplifier 27 receives echo signals 22a from the transducer 12, and passes these to a digitizer 29 for analogue-digital conversion. The digitised signals are passed to a signal processor 30 (which may be incorporated within a personal computer. The signal processor 30 may include, or be coupled to an appropriate image processing device 31, which also may be incorporated within a personal computer. An analogue filter 28 may be incorporated in the receive path, e.g. before and/or after amplification of the received echo signals. It will be understood that any or all of the elements 27-30 of the receive sub-system 22 could be combined and/or incorporated into a single electronic circuit.

In a practical implementation, a flow phantom was constructed by creating a 1 mm flow channel through tissue mimicking phantom, and contrast agent was passed through this 'vessel' during the experiments. The contrast agent employed was an experimental phospholipid-stabilized composition prepared according to example 1$i$ of WO 2004/069284. Images were constructed by pulse-inversion techniques from a series of pulse ensembles (10 or 25% bandwidth) acquired during continuous translation. The pulse-inversion technique effects cancellation of linear signals by exploiting differences in consecutive phase-inversed pulses due to nonlinear propagation or bubble responses. If there is substantial motion between the tissue and transducer between pulses, this will result in inefficient cancellation of the fundamental frequency.

In a first experiment, a needle-mounted IVUS transducer was employed (having a bandwidth of 15 to 45 MHz) to image free bubbles flowing freely through the vessel. The vessel was first imaged in 20 MHz fundamental mode (F20), which is linear imaging. The vessel was then imaged using the second harmonic of a 20 MHz transmit pulse (H40), and finally using the subharmonic of a 40 MHz transmit pulse, centred closer to 20 MHz (S20).

In a second experiment, the potential to image bound microbubbles in a nonlinear manner at high frequencies was demonstrated. This was done by passing contrast agent through a phantom vessel composed of a material that bound to the agent in a non-specific manner. After flushing the phantom with distilled water, the inner part of the phantom was coated in a layer of bound bubbles. Imaging in this experiment was done with a spherically focused polymer transducer of centre frequency 19 MHz, using a transmit frequency of 20 MHz. Imaging was done in both F20 mode and using the subharmonic (SH10) emissions.

Figure 5:
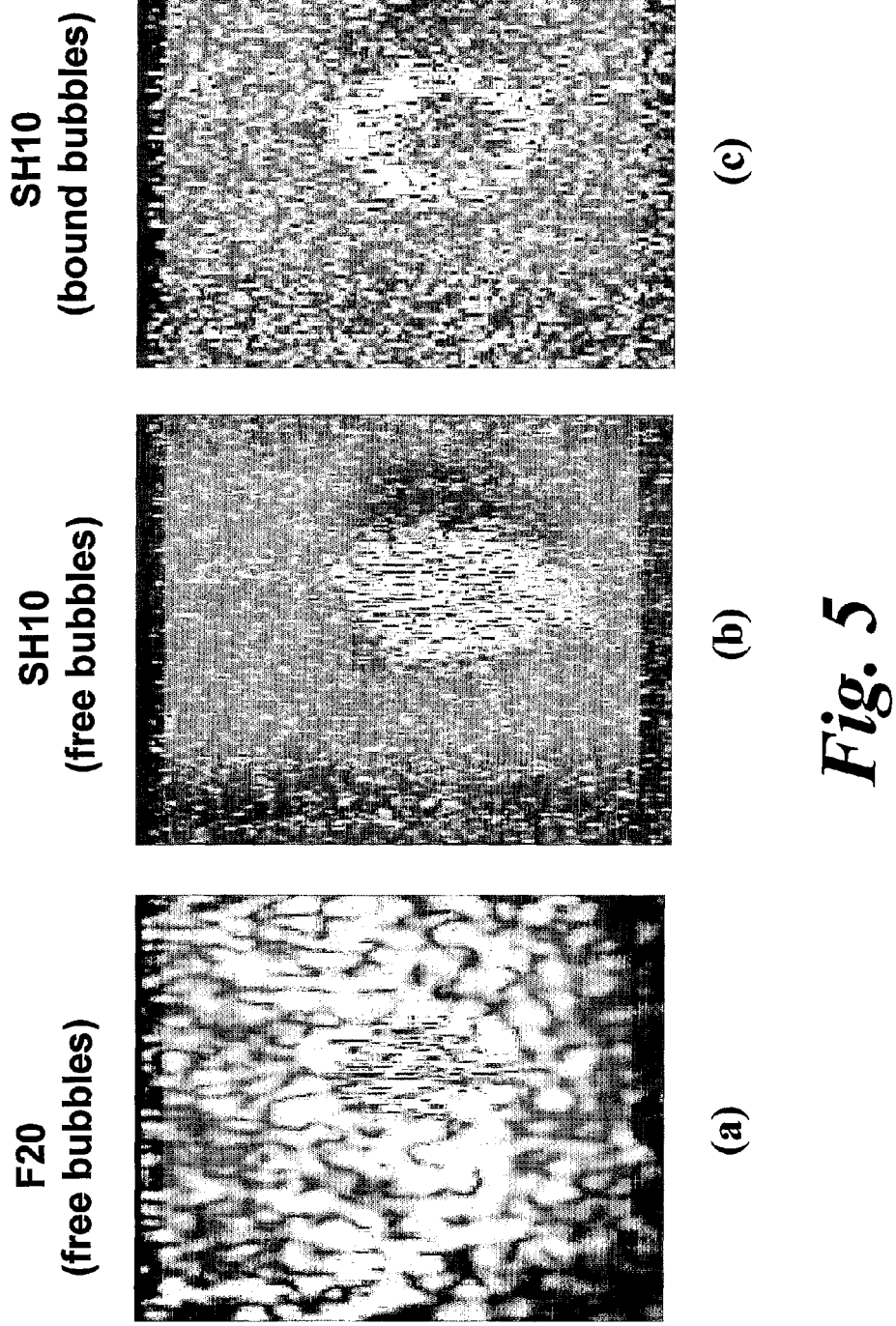
FIG. 5 shows exemplary images of free and bound contrast agent bubbles produced using: (a) 20 MHz fundamental frequency imaging of free bubbles; (b) 10 MHz subharmonic imaging of free bubbles; and (c) 10 MHz subharmonic imaging of bound bubbles.

The results are shown in FIGS. 3 to 5.

As shown in FIG. 3, F20 imaging shows little contrast between tissue and agent flowing in the vessel (FIG. 3a). At low transmit amplitudes (FIG. 3b), H40 was found to produce improvements in contrast to tissue signal ratios (CTR). At higher transmit amplitudes (FIG. 3b), the CTR degrades due to increases in nonlinear propagation giving rise to a stronger tissue harmonic signal. This indicates that lower pressure ranges will be appropriate for contrast agent imaging, and higher pressure amplitudes are appropriate for tissue harmonic imaging.

As shown in FIG. 4, the fundamental frequency image, F40 (FIG. 4a) offers poor visualization of the vessel. In SH20 mode results indicate tissue suppression approaching the noise floor, with up to 18 dB of contrast to noise ratio at higher transmit amplitudes. These results indicate the feasibility of nonlinear contrast imaging with IVUS. The feasibility to suppress tissue signals is critical in reliably detecting vasa vasorum with IVUS.

Referring to FIG. 5, FIG. 5a shows F20 imaging of free flowing bubbles, figure 5b shows SH10 imaging of free flowing bubbles, and FIG. 5c shows SH10 imaging of bound bubbles. These results demonstrate that nonlinear targeted contrast imaging is viable at high frequencies from the perspective of bound-agent detection using catheter-based transducers.

The imaging techniques using a catheter-based ultrasound probe may be used to assist in localised drug delivery by providing real-time image guidance to the drug delivery mechanism.

The drug delivery mechanism may be incorporated with the contrast agent. Drugs or genetic material may be incorporated into, located within or in some manner attached to or imbedded in the contrast agent. The catheter-based IVUS transducer can be used to assess an appropriate location for drug or genetic material delivery and to facilitate its delivery. The delivery may be facilitated by the acoustic stimulation of either the imaging transducer or the second lower frequency transducer, if present. The acoustic stimulation may effect the disruption of contrast agent which contains drug or genetic material, or contrast agent that is in the presence of drug or genetic material. This may involve the stimulation of oscillations of contrast agent which contains drug or genetic material, or contrast agent that is in the presence of drug or genetic material, in a manner that facilitates the delivery of the drug or genetic material to the tissue or cells of interest. In a preferred embodiment, a two transducer approach is employed such that the lower frequency (1 to 15 MHz transducer) is used to facilitate the delivery of drug or genetic material, and the second transducer, the imaging transducer, being used to guide or monitor the treatment procedure.

With further reference to FIG. 1, the contrast agent delivery system using conduit 17b formed by sheath 17 may also be configured with means for applying a saline (or heparinized saline) flush between contrast injections. The delivery system conduit may also be provided with a means (not shown) for displacing a smaller volume of agent to the catheter tip, particularly if the volume of the catheter sheath 17 may exceed the desired injection volume.

In a simple case, existing syringe adaptors may be used to manually introduce the agent and saline flushes. An exemplary automated implementation consists of a two-plunger syringe pump (one for a saline syringe and the second for the agent). The agent injection volume and injection rate can be specified and the agent can then automatically be pushed slowly (to avoid pressurization of agent that would cause its disruption) towards the catheter tip. This can then be followed by the bolus injection phase (the timing of which may be electronically synchronised with the IVUS imaging and acquisition system.

A summary of the presently preferred operating parameters for both transmission of excitation signals and reception/processing of echo signals is now provided for the various catheter-based ultrasonic contrast imaging schemes described.

For second harmonic tissue and contrast agent imaging techniques deploying a single element transducer, pulse centre frequencies in the range of 15 to 30 MHz, with total pulse frequency content between 5 and 60 MHz is preferred. Peak positive acoustic pressures within the beam (as measured in a water tank) lie between 5 kPa and 1 MPa for contrast imaging mode. Peak positive acoustic pressures within the beam (as measured in a water tank) lie between 100 kPa and 10 MPa when operating in tissue harmonic imaging mode.

For subharmonic imaging techniques using a single element transducer, pulse centre frequencies in the range of 30 to 60 MHz, with total pulse frequency content between 10 and 80 MHz is preferred. Peak positive acoustic pressures within the beam (as measured in a water tank) lie between 20 kPa and 8 MPa when operating in contrast imaging mode.

In a power modulation mode, pulse centre frequencies in the range of 20 to 50 MHz, with total pulse frequency content between 10 and 80 MHz is preferred.

Peak positive acoustic pressures within the beam (as measured in a water tank) lie between 5 kPa and 8 MPa when operating in contrast imaging mode.

In other nonlinear oscillation modes (e.g. using time dependant signals such as transients or using pulse-length dependant effects), pulse centre frequencies in the range of 20 to 50 MHz, with total pulse frequency content between 10 and 80 MHz is preferred. Peak positive acoustic pressures within the beam (as measured in a water tank) lie between 5 kPa and 8 MPa.

In a destruction pulse mode using a single element transducer, transmit centre frequencies in the range of 10 to 40 MHz, with pulse bandwidths between 0.1% and 50%—6 dB relative bandwidths are preferred. Peak positive acoustic pressures within the beam (as measured in a water tank) lie between 100 kPa and 15 MPa.

In a destruction pulse mode using a separate low frequency element to destroy contrast agent, pulse centre frequencies in the range of 1 to 15 MHz, with pulse bandwidths lying between 0.1% and 50%—6 dB relative bandwidths are preferred. Peak positive acoustic pressures within the beam (as measured in a water tank) lie between 100 kPa and 15 MPa.

For a non-destructive dual element imaging mode using a separate low frequency element to initiate oscillations, pulse centre frequencies in the range of 1 to 15 MHz, with pulse bandwidths between 0.1% and 50%—6 dB relative bandwidths are preferred. Peak positive acoustic pressures within the beam (as measured in a water tank) lie between 100 kPa and 5 MPa.

For a non-destructive dual element imaging mode using both low and high frequency elements to initiate contrast agent oscillations, pulse centre frequencies for the low frequency element in range of 1 to 15 MHz and pulse centre frequencies for high frequency element in range of 15 to 50 MHz, with pulse bandwidths between 0.1% and 20%—6 dB relative bandwidths are preferred. Peak positive acoustic pressures within the beam (as measured in a water tank) lie between 100 kPa and 5 MPa.

For basic contrast agent detection, with a single element transducer system, agent detection is achieved by means of the nonlinear behaviour of bubbles. The nonlinear signals are isolated by means of filtering and analysis of pulse sequences. Individual transmitted pulses have characteristics that fall within the range of those described above. The expression 'pulse sequence' refers to a sequence of potentially different pulses that are transmitted and received as the transducer is rotating.

In the simplest case, all transmitted pulses are identical and sent at equal intervals in the range of 1 ms to 0.001 ms. Nonlinear echo signals at subharmonic or second harmonic frequencies are isolated by a combination of analog and digital filtering of the individual received echo signals. A single IVUS image is formed by taking the envelope of individual RF lines displayed in a linear, logarithmic or other compression scheme. In general, the signals from a group of adjacent pulses (more than two) are combined to form an image line, and in doing so benefit from signal averaging effects. The combination may take the form of direct averaging of the time domain, or power averaging or another scheme.

Transmitted pulses may also be phase-inversed (i.e. have 180 degree phase differences) with respect to each other. A group of these pulses (two or more) may be combined to form an image line as a strategy for removing linear tissue signals. The operation to combine the pulses may take different forms, only one of which is to sum with equal weighting all the pulses.

Transmitted pulses may also be phase shifted with respect to each other by an amount other than 180 degrees (e.g. 90 degrees). A group of these pulses (two or more) may be combined to form an image line as a strategy for removing linear tissue signals. The operation to combine the pulses may take different forms, only one of which is to sum with equal weighting all the pulses.

Pulses may be transmitted with different amplitudes, referred to as power modulation. This will vary the amount of nonlinear bubble behaviour. A group of these pulses (two or more) may be combined to form an image line as a strategy for removing linear tissue signals. The operation to combine the pulses may take different forms. For example, if two pulses are transmitted, the first with half the amplitude of the second, then the received pulse pair is added by multiplying the first pulse by two before subtracting it from the second.

Transmitted combinations of phase and amplitude modulation may be used to isolate nonlinear signals.

Transmit pulse lengths may be varied. The received signals may then be processed to extract nonlinear transients or other pulse length dependant signals arising from bubble oscillations.

Transmit frequency may be varied within a pulse. The received signals may then be processed to extract signals arising from bubble oscillations.

Formation of images from the imaging transducer received signals when the transmit pulses are sent out by either the imaging transducer or a separate low frequency transducer to destroy agent may be effected in several ways, both for when destructive pulses are transmitted by the imaging transducer, or by a separate low frequency transducer.

For pulse sequences that consist of one or more destructive pulses following by imaging pulses of the types described above, one or more entire rotations of the IVUS element can be conducted during which time high amplitude pulses are sent with the intention of destroying free or targeted agent with either transducer. Following the destructive frames, imaging is then performed using one of the methods described above. This can be used as a means of implementing destruction-reperfusion imaging or to assess re-accumulation of targeted agent.

If the above are conducted following the injection of a bolus, the changes of signals as a function of time in regions of interest may be used to differentiate agent located in vasa vasorum or targeted agent from free agent within the main lumen.

With targeted agent, a different pressure, bandwidth and frequency range may be employed as a means of distinguishing targeted agent from bound agent.

Pulse sequences may consist of non-destructive (or predominantly non-destructive) pulses sent on the low frequency transducer and nonlinear signals detected by the imaging transducer. These signals may include superharmonics, ultraharmonics or transients.

Pulse sequences may consist of the simultaneous transmitting of different pulses on both the imaging transducer and the low frequency transducer.

The same apparatus as described herein is capable of operating in tissue (including blood) imaging mode. By being able to operate in either mode it is possible to superimpose contrast specific signals onto tissue structural images. Tissue signals may be isolated from the incoming received signals (which may also contain contrast-specific signals) through processing. Alternatively, tissue signals may be extracted from modifications of the pulse sequences (i.e. both transmit pulse characteristics and amplitudes) that would allow for tissue imaging pulses to be interleaved with contrast imaging pulses. Tissue imaging can be performed in linear or nonlinear imaging modes. Multiple pulse techniques such as pulse-inversion imaging or amplitude modulation can also be applied to nonlinear tissue imaging (both in the presence of contrast agent or not). For tissue imaging the multiple pulse techniques will be optimised so that the level of harmonics generated are maximized, or are maximized after a certain distance, or to maximize the contrast in between tissue components.

This may also be accomplished by alternating frames to be dedicated to either contrast or tissue signals. It is recognized that higher amplitude transmit conditions will favour tissue second harmonic imaging, and lower transmit amplitudes will favour contrast second harmonic imaging. Tissue superharmonic imaging may also be performed.

In a practical implementation, tissue harmonic imaging was illustrated on a continuously rotating single element transducer in a tissue mimicking phantom and in an atherosclerotic rabbit aorta. Gaussian enveloped pulses at centre frequencies of either 20 MHz or 40 MHz were generated. The fractional bandwidth of the pulses was 25%. In the phantom and in vivo experiments we acquired results of the fundamental 20 MHz mode (F20), the fundamental 40 MHz mode (F40) and the harmonic 40 MHz mode (H40), i.e. the second harmonic of 20 MHz. In these experiments averaging of neighbouring lines to increase the signal-to-noise ratio (SNR) was used. Harmonic images (H40 mode) were made by means of pulse inversion. This multiple pulse technique has not been used with rotating single-element IVUS catheters before and is counterintuitive because of loss of correlation due to lateral motion.

Figure 6:
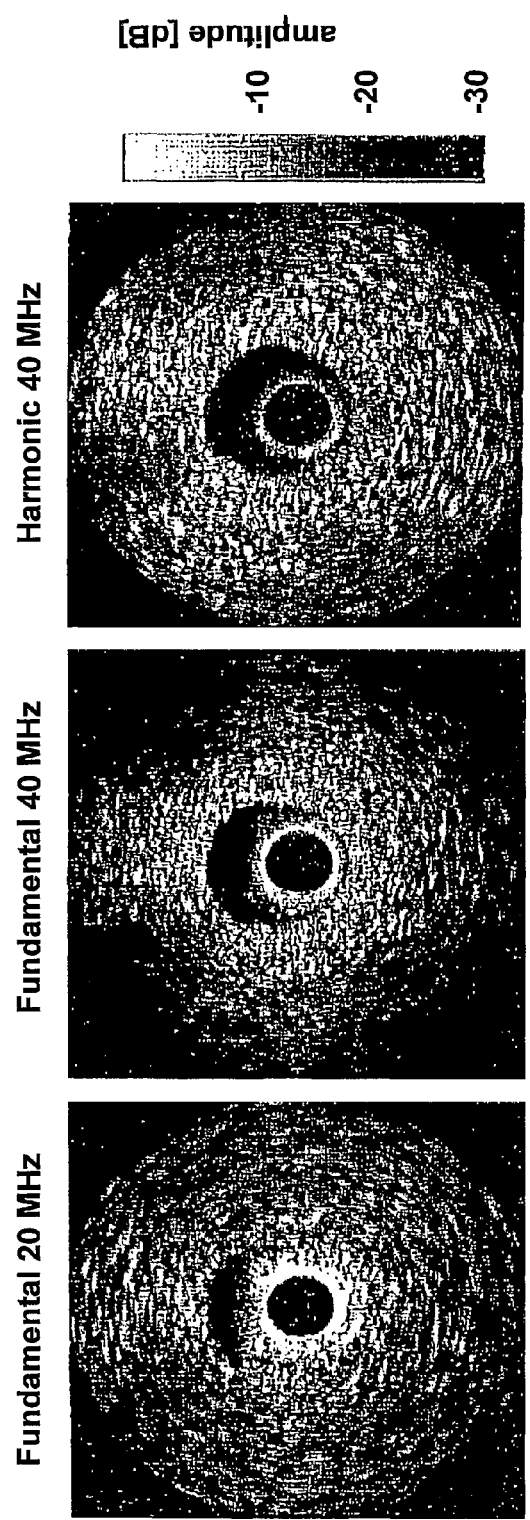
FIG. 6 shows exemplary images of cross-sections of a tissue mimicking phantom acquired with the fundamental 20

With reference to FIG. 6, tissue harmonic imaging using pulse inversion has shown to be feasible in a tissue mimicking phantom and to improve image quality.

With reference to FIG. 7, tissue harmonic imaging using pulse inversion has shown to be feasible in vivo and to improve image quality.

Other embodiments are intentionally within the scope of the accompanying claims.

REFERENCES

[1] F Forsberg et al, "Subharmonic imaging of contrast agents", *Ultrasonics*, vol. 38, pp. 93-98, March 2000.

[2] G M Lanza et al, "Targeted ultrasonic contrast agents for molecular imaging and therapy", Prog. Cardiovasc. Dis., vol. 44, pp. 13-31, 2001

[3] S M Demos et al, "In vivo targeting of acoustically reflective liposomes for intravascular and transvascular ultrasonic enhancement", *Journal of the American College of Cardiology*, vol. 33(3), pp. 867-875, 1999

[4] C Cachard et al, "Ultrasound contrast agent in intravascular echography: An in vitro study", *Ultrasound in Medicine and Biology*, vol. 23 (5), pp. 705-717, 1997

[5] C M Moran et al, "In vitro acoustic characterization of ultrasonic contrast agents at 30 MHz", *Ultrasound Med. Biol.*, vol. 28, pp. 785-791, 2002

[6] C X Deng et al, "Imaging and spectrum analysis of contrast agents in the in vivo rabbit eye using very high frequency ultrasound", *Ultrasound Med. Biol.*, vol. 24, pp. 383-394, 1998

[7] D E Goertz, "High frequency ultrasound imaging of the microcirculation", Ph. D. Thesis, University of Toronto, 2002

[8] D Kruse et al, "High frequency ultrasound with an eigendecomposition filter to assess the effect of laser cyclophotocoagulation treatment on blood flow", *Proc. IEEE Ultrason. Symp.*, pp. 49-50, 2002

[10] D B Khismatullin et al, "Radial oscillations of encapsulated microbubbles in viscoelastic liquids", *Phys. Fluids*, vol. 14(10) pp. 3534-3557, 2002

[11] D E Goertz et al, "Non-linear scattering properties of microbubble contrast agents at high frequencies", *Proc. IEEE Utrason. Symp.*, 2001

[12] D E Goertz et al, "High frequency nonlinear B-scan imaging of microbubble contrast agents", in press, *IEEE Trans. Ultrason., Ferroelec., Freq. Contr.*, 2004

[13] A F W van der Steen et al, "Harmonic imaging at high frequencies for IVUS", *Proc. IEEE Ultrason. Symp.*, pp. 1537-1540, 1999

[14] M E Frijlink et al, "High frequency harmonic imaging in the presence of intravascular stents", *Proc. IEEE Ultrason. Symp.*, pp. 208-211, 2003.

[15] D E Goertz et al, "The effect of bubble size on nonlinear scattering at high frequencies", *Proc. IEEE Ultrason. Symp.*, pp. 1503-1507, 2003

The invention claimed is:

1. ultrasound imaging device for detecting internal properties of a target body, comprising:
   a rotatable ultrasound first transducer positioned at a distal end portion of a catheter for intravascular introduction into the target body, the rotatable ultrasound first transducer having a transmit frequency;
   a waveform generator, coupled to the rotatable ultrasound first transducer, for producing excitation pulses at the transmit frequency and configured to generate multiple pulse sequences during rotation of the rotatable ultrasound first transducer comprising any one of phase shifted, phase inverted or power modulated multipulse sequences for stimulating echo signals at one or more of the harmonic and subharmonic frequencies during said rotation of the rotatable ultrasound first transducer;
   a receiver for receiving echo signals from the rotatable ultrasound first transducer;
   a signal processor for analyzing echo signals from the rotatable ultrasound first transducer at said one or more harmonics and subharmonics of the transmit frequency and generating images therefrom; and
   a lower frequency second transducer positioned at the distal end portion of the catheter for producing contrast-agent destruction pulses in the range of 1 to 15 MHz;
   wherein the ultrasound imaging device is configured to enhance contrast agent to tissue signals using the one or more phase shifted, phase inverted and power modulated multipulse sequences as nonlinear imaging techniques, whereby in use the images are generated using echo signals from the rotatable ultrasound first transducer while the contrast-agent destruction pulses are produced using the lower frequency second transducer.

2. The ultrasound imaging device of claim 1 in which the rotatable ultrasound first transducer and waveform generator are adapted to transmit excitation signals at a frequency in the range 10 to 80 MHz.

3. The ultrasound imaging device of claim 1 in which the rotatable ultrasound first transducer and waveform generator are adapted to transmit excitation signals having a centre frequency in the range 15 to 50 MHz.

4. The ultrasound imaging device of claim 1 in which the rotatable ultrasound first transducer has an active element surface of less than 1 mm diameter.

5. The ultrasound imaging device of claim 1 in which the rotatable ultrasound first transducer is adapted to produce a steerable excitation beam.

6. The ultrasound imaging device of claim 5 in which the rotatable ultrasound first transducer comprises at least one mechanically steerable active element.

7. The ultrasound imaging device of claim 5 in which the rotatable ultrasound first transducer comprises an array of active elements which can be phased to result in electronic beam steering.

8. The ultrasound imaging device of claim 1 in which the rotatable ultrasound first transducer is adapted to produce acoustic pressures of at least 10 kPa at the transmit frequency.

9. The ultrasound imaging device of claim 8 in which the rotatable ultrasound first transducer is adapted to produce acoustic pressures of at least 100 kPa at the transmit frequency.

10. The ultrasound imaging device of claim 1 in which the lower frequency second transducer is adapted to produce acoustic pressures of at least 200 kPa.

11. The ultrasound imaging device of claim 1 in which the signal processor includes means for determining the energy at the one or more harmonic and subharmonic frequencies by analysis of multiple pulse sequences.

12. The ultrasound imaging device of claim 1 further comprising:
   a contrast agent delivery conduit extending along the catheter, the delivery conduit having an exit orifice proximal to the catheter-based ultrasound first transducer.

13. The ultrasound imaging device of claim 12 further including a delivery pump for delivering a predetermined volume of contrast agent through the exit orifice.

14. The ultrasound imaging device of claim 12 further including a delivery pump for delivering contrast agent through the exit orifice at a predetermined rate.

15. The ultrasound imaging device of claim 12 further including a remotely controlled closure mechanism to open and close the exit orifice.

16. The ultrasound imaging device of claim 12 in which the exit orifice and an active surface of the catheter-based ultrasound first transducer are separated by a distance of between 10 and 300 mm.

17. The ultrasound imaging device of claim 12 further including a bend in the distal end region of the catheter to provide lateral displacement of the catheter-based ultrasound first transducer to a position off the axis of a main portion of the catheter.

18. The ultrasound imaging device of claim 1 in which
the waveform generator is configured to generate excitation pulses, in said multiple pulse sequences, that are phase shifted with respect to each other, and
the signal processor is configured to combine pulses to form an image line to remove linear tissue signals.

19. The ultrasound imaging device of claim 1 in which
the waveform generator is configured to generate multiple pulse sequences that are phase and amplitude modulated, and
the signal processor is configured to combine pulses to isolate non-linear echo signals.

20. The ultrasound imaging device of claim 1 in which
the waveform generator is configured to generate excitation pulses, in said multiple pulse sequences, that are power modulated, and
the signal processor is configured to combine pulses to form an image line to remove linear tissue signals.

21. The ultrasound imaging device of claim 18, claim 20 or claim 19 in which the signal processor is configured to combine signals from a group of adjacent pulses to form an image line by averaging in the time domain or power averaging.

22. An ultrasound imaging device for intravascular ultrasound imaging of a patient's body comprising:
a rotatable catheter-based ultrasound first transducer for insertion into the body at a site of interest, the catheter-based ultrasound first transducer having a transmit frequency;
means for transmitting at the transmit frequency a series of ultrasound excitation signals from the catheter-based ultrasound first transducer comprising any one of phase shifted, phase inverted or power modulated multipulse sequences sufficient to induce a non-linear response (a) in tissue at the site of interest in the body (b) at one or more of the harmonic and subharmonic frequencies during rotation of the catheter-based ultrasound first transducer;
means for receiving ultrasound echo signals in response to the excitation signals;
means for generating an image of the site of interest in the body using non-linear components of the received ultrasound echo signals at said one or more harmonics and subharmonics of the transmit frequency, whereby the ultrasound imaging device enhances contrast agent to tissue signals using the phase shifted, phase inverted or power modulated multipulse sequences as nonlinear imaging techniques; and
a lower-frequency second transducer with the catheter-based ultrasound first transducer for producing contrast-agent destruction pulses in the range of 1 to 15 MHz;
wherein the ultrasound imaging device is configured to generate the image using the echo signals from the catheter-based ultrasound first transducer while producing the contrast-agent destruction pulses using the lower-frequency second transducer.

23. A method of intravascular ultrasound imaging of a patient's body comprising the steps of:
introducing both a rotatable catheter-based ultrasound first transducer and a second transducer into the body at a site of interest, the catheter-based ultrasound first transducer having a transmit frequency greater than a 1 to 15 MHz frequency range of contrast-agent destruction pulses produced by the second transducer;
transmitting at the transmit frequency a series of ultrasound excitation signals from the catheter-based ultrasound first transducer comprising any one of phase shifted, phase inverted or power modulated multipulse sequences sufficient to induce a non-linear response (a) in tissue at the site of interest in the body (b) at one or more of the harmonic and subharmonic frequencies during rotation of the catheter-based ultrasound first transducer;
receiving ultrasound echo signals in response to the excitation signals; and
generating an image of the site of interest in the body using non-linear components of the received ultrasound echo signals at said one or more harmonics and subharmonics of the transmit frequency;
whereby contrast agent to tissue signals are enhanced using the phase shifted, phase inverted or power modulated multipulse sequences as nonlinear imaging techniques, and the image is generated using the echo signals from the catheter-based ultrasound first transducer while the contrast-agent destruction pulses are produced using the second transducer.

24. The method of claim 23 wherein the catheter-based ultrasound first transducer is a rotating single element transducer.

25. The method of claim 23 in which the second transducer produces acoustic pressures of at least 200 kPa.

* * * * *